United States Patent
Heidsieck et al.

(10) Patent No.: US 6,592,257 B1
(45) Date of Patent: Jul. 15, 2003

(54) DETACHABLE DEVICE FOR RADIOLOGICAL DIGITAL IMAGING

(75) Inventors: Robert Heidsieck, Rocquencourt (FR); Vincent Rit, Douai (FR); Catherine Picard, Magny les Hameaux (FR); Jean Louis Baudet, Bourg-la-Reine (FR)

(73) Assignee: GE Medical Systems, SA, Buc (FR)

( * ) Notice: Subject to any disclaimer, the term of this patent is extended or adjusted under 35 U.S.C. 154(b) by 0 days.

(21) Appl. No.: 09/254,697

(22) Filed: Jun. 11, 1999

Related U.S. Application Data

(63) Continuation of application No. PCT/FR97/01665, filed on Sep. 22, 1997.

(30) Foreign Application Priority Data

Sep. 24, 1996 (FR) ............................................. 96 11610

(51) Int. Cl.$^7$ ................................................ H05G 1/64
(52) U.S. Cl. ........................ 378/189; 378/98.8; 378/37
(58) Field of Search .............. 378/98.8, 169, 378/181, 182, 187, 37, 189

(56) References Cited

U.S. PATENT DOCUMENTS

| | | | | |
|---|---|---|---|---|
| 5,440,130 A | * | 8/1995 | Cox et al. | 250/370.09 |
| 5,594,769 A | * | 1/1997 | Pellegrino et al. | 378/37 |
| 5,661,309 A | * | 8/1997 | Jeromin et al. | 250/580 |
| 5,715,292 A | * | 2/1998 | Sayag et al. | 378/98.8 |
| 5,773,832 A | * | 6/1998 | Sayed et al. | 250/370.09 |
| 5,844,961 A | * | 12/1998 | McEvoy et al. | 378/98.8 |
| 5,925,890 A | * | 7/1999 | Van den Bogaert | 250/580 |
| 6,173,035 B1 | * | 1/2001 | Tachibana et al. | 378/39 |
| 6,208,708 B1 | * | 3/2001 | Hoheisel et al. | 378/37 |
| 6,213,637 B1 | * | 4/2001 | Leidenberger | 378/189 |

FOREIGN PATENT DOCUMENTS

| | | |
|---|---|---|
| DE | 4403930 | 8/1995 |
| EP | 0714038 | 5/1996 |

* cited by examiner

Primary Examiner—Drew A. Dunn
Assistant Examiner—Allen C Ho
(74) Attorney, Agent, or Firm—Jay L. Chaskin

(57) ABSTRACT

Removable digital X-ray imaging device intended for mammography, comprising X-ray detectors placed on one edge of the device upon imaging. The device contains box for protecting the X-ray detectors by separating the X-ray detectors from the edge of the device, the device being in rest position.

26 Claims, 3 Drawing Sheets

DETACHABLE DEVICE FOR RADIOLOGICAL DIGITAL IMAGING

This is a continuation application of International Application No. PCT/FR97/01665 filed Sep. 22, 1997.

BACKGROUND OF THE INVENTION

The present invention concerns a removable digital device designed for radiography, e.g., for X-ray mammography. Such an imaging device is intended to be inserted in an X-ray machine containing an X-ray source, a means of holding the organ X-rayed and a removable imaging device.

Mammography devices are known, for example, which include an X-ray source arranged on one side of the organ to be X-rayed, a supporting table transparent to X-rays, arranged on the other side of the organ to be X-rayed, an adjustable holding platform that applies the organ on the supporting table and a housing for receiving an imaging cassette containing an exposable film.

The housing is placed in the supporting table.

After an image of the organ has been taken, the cassette containing the exposed film is extracted from its housing and the film is developed.

Such devices are used, in general, to search for possible breast cancer symptoms. A first operation consists of a systematic screening which only necessitates taking one or two films. If those films reveal cancer symptoms, a more thorough diagnosis is then undertaken, requiring a greater number of films, for example, of a particular area of the organ, using the method of image representation and visualization.

If the diagnosis reveals the presence of a cancer, it may be necessary to take a biopsy. A puncture system is then placed on the X-ray machine. The puncture system generally comprises a needle for taking the specimen in an area suspected of being cancerous, for purposes of analysis, and a needle holder. The X-ray machine then serves to secure the positioning of the needle. The puncture system can also be used for placing a hook equipped with a wire intended for marking by the surgeon of a cancerous area upon an operation.

On use of a puncture system, a first film is taken for centering of the area to be punctured and then, thanks to an X-ray source tilting mechanism, one film with a +15° angle and a second film with a −15° angle are taken for the purpose of obtaining by stereotaxis the three-dimensional coordinates of a particularly significant point and then, after the needle enters the organ, at least two control films are taken to verify that the needle is in place in the area to be punctured. In practice, a total of approximately eight x-rays are taken on use of the puncture system. The development of an exposable film takes from 3 to 5 minutes per X-ray.

Throughout the time of the biopsy operation and development of the films, the organ remains absolutely immobile in relation to the X-ray machine and is kept compressed between the table and the holding platform. The patient must therefore remain for over 30 minutes in an immobile and relatively uncomfortable position.

With a view to reducing the time of immobilization of the organ, the cassettes containing exposable films can be replaced by cassettes containing digital imaging means capable of extremely rapid imaging. The biopsy operations are thus much shorter and reduce the discomfort of those examinations. Furthermore, the digital imaging cassettes make possible an improvement of quality of the diagnosis.

For economic reasons, it is desirable to use digital imaging cassettes without changing the rest of the X-ray machine. The cassette must be removable, so that it can be placed either under the table upon a diagnosis or in the puncture system upon a biopsy.

A digital imaging cassette comprises a casing inside which an X-ray signal detection device is placed. That device can, for example, contain a scintillator capable of converting the incident X-radiation into luminous radiation, an optical fiber making it possible to filter most of the X-radiation having crossed the scintillator and protecting the components situated between said optical fiber and a matrix camera with charge transfer elements (CCD) forming a sensitive zone. That detection device is relatively cumbersome and fragile. Now, it is indispensable to obtain an image of the organ X-rayed as close as possible to the patient's chest. The sensitive zone of the cassette must therefore be placed on one edge of the latter so as to come in proximity to the patient's chest.

The disadvantage of this type of cassette, whose sensitive, fragile and cumbersome area is situated on an edge, is the risk of damage, for example, by impact on the sensitive area, upon handling of the cassette by an operator.

BRIEF SUMMARY OF THE INVENTION

This invention concerns a device whose sensitive area is protected against mechanical shocks when the cassette is not in service, while making it possible to obtain an image of the organ taken as close as possible to the chest.

The removable digital X-ray imaging device in an embodiment of the invention includes X-ray detectors placed on the edge of the device upon imaging. The digital imaging device includes means for protecting the X-ray detectors by separating said detectors from the edge of the device, the latter being in rest position.

BRIEF DESCRIPTION OF THE DRAWING(S)

The invention will be better understood by study of the detailed specification of some embodiments taken by way of nonlimitative example and illustrated by the attached drawings, on which:

DETAILED DESCRIPTION OF THE INVENTION

Figure 1:
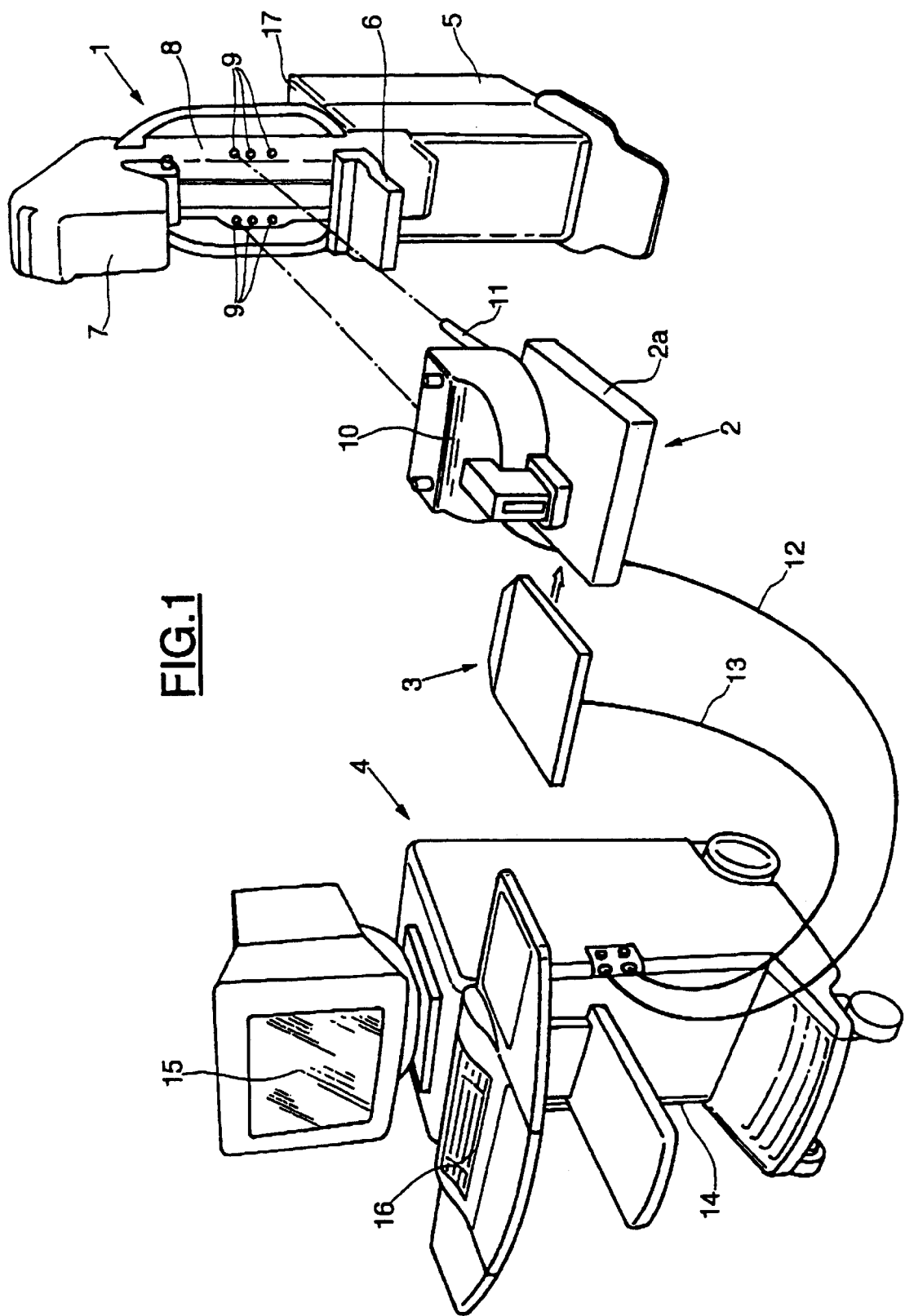
FIG. 1 is an overall view in perspective of the mammography system.

In an embodiment of the invention, the imaging device comprises a roughly parallelepipedal box bearing X-ray detectors, said detectors being arranged inside the box and on one of the sides of the latter.

In an embodiment of the invention, the imaging device comprises a case provided with an open face and capable of receiving the box, the side of the box integral with the detectors being capable of coming in contact with the face of the case opposite said open face. An X-ray can thus be taken as close as possible to the patient's chest.

In an embodiment of the invention, the imaging device comprises elastic means arranged between the bottom of the case formed by the face opposite the open face and the side of the box integral with detectors for separating the box from the bottom of the case in rest position, said side of the box being capable of entering in contact with the bottom of the case, the elastic means not abutting. Thus, upon a shock due to handling, the box can be shifted in relation to the case, thus reducing the acceleration due to the shock sustained by the detectors. The box can include at least one housing of the elastic means formed by at least one spring.

The side of the box opposite the side integral with the detectors preferably projects from the open face of the case, the device being in rest position.

In an embodiment of the invention, the box is capable of being shifted by translation relative to the case.

In another embodiment the box is capable of being shifted relative to the case by pivoting around a corner of the box in contact with the bottom of the case.

In an embodiment of the invention the means for converting the X-rays into electric signals comprise a scintillator capable of converting the x-rays into visible light radiation, an optical fiber and a CCD matrix camera.

The X-ray system in an embodiment of the invention includes an imaging device, an X-ray emission means, an imaging device support, the organ to be X-ray being arranged between the support and the emission means and a signal control and processing means connected to the imaging device for reading the images obtained. In an embodiment of the invention, the system further includes means for taking a biopsy of the organ X-rayed.

In the embodiment of the invention, one obtains an X-ray system capable of supplying images of the X-rayed organ in a very short time span, while making possible an improvement of the quality of diagnosis at a reduced cost of use.

As illustrated on the figures, the mammography system comprises a mammogram machine, a puncture system 2, a digital imaging cassette 3 and control and processing means 4. The X-ray machine contains a base 5 standing on the floor and supporting a breast-holding platform 6 of adjustable height and an X-ray source 7 which can be tilted ±15° from the vertical plane of symmetry of the X-ray machine 1. The X-ray source 7 is supported by a column 8 provided on its front face with a plurality of holes 9 for fastening the puncture system 2.

The puncture system 2 can be mounted or not on the X-ray machine and contain a holding platform 2a serving as a compression pad, a needle holder 10 and a needle, not represented, capable of performing a biopsy in the organ to be X-rayed. The puncture system 2 is equipped with two pins 11, only one of which is visible in FIG. 1, capable of being accommodated in the holes 9 of the column 8 of the mammogram machine 1, and with fastenings, not represented, on the column 8. The puncture system 2 is connected by an electric cable 12 to the control and processing means 4.

The digital imaging cassette 3 is flat and appreciably parallellepipedal and is connected by an electric cable 13 to the control and processing means 4.

The control and processing means 4 comprise a frame 14 and electronic means, not represented, connected to the puncture system 2 and to the cassette 3 respectively by the electric cables 12 and 13 in order to process the information received from the cassette 3 and to control the puncture system 2 and, in particular, movement of the needle holder 10 upon a biopsy. The control and process means 4 also include a screen 15 displaying the images of the organ X-rayed and a keyboard 16. The control and processing means 4 can be equipped with software designed for calculation of the three-dimensional coordinates of points of the X-rayed organ from two images taken at different angles thanks to pivoting of the X-ray source 7. An excellent visualization can then be obtained of particular areas of the X-rayed organ upon a diagnosis, as well as of the positioning of the needle in the X-rayed organ upon a biopsy, by using optimized display methods.

The cassette 3 can, following the direction of the arrow of FIG. 1, enter a housing of the puncture system 2 or a housing provided in a cassette holder, not represented, used on diagnostic examinations and arranged to be fastened on a breast-holding platform 6, or even in rest position, in a storage space 17 of the mammogram machine 1. Providing a storage space 17 on the mammogram machine 1 makes it possible to use a short cable 13 and thus reduce the risks of falling and damage to the cassette 3.

Figure 2:
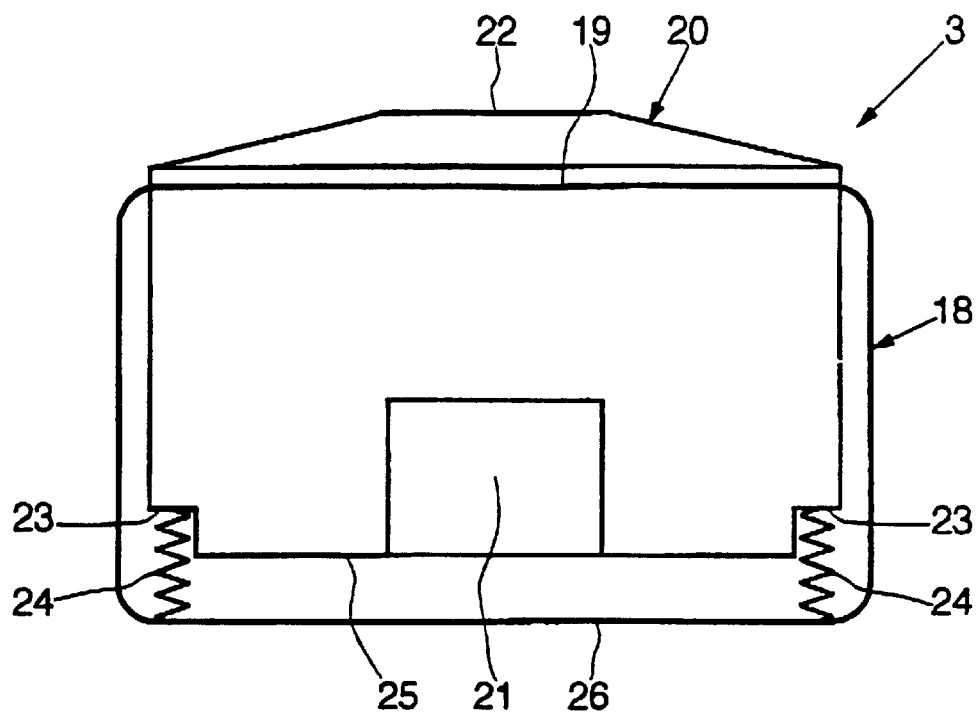
FIG. 2 is a top view in elevation of the imaging device in rest position.

As illustrated in FIG. 2, the cassette 3 comprises a thin case 18, appreciably parallelepipedal and provided with an open face 19. Inside the case 18, a box 20 of suitable dimensions is housed. The box 20 contains a sensitive zone 21, a portion 22 projecting from the open face 19 of the case 18 and two housings 23 of springs 24. The housings 23 are provided on the face 25 of the box 20 opposite the projecting portion 22. The two helical springs 24 are placed between the bottom 26 of the case 18 and the housings 23 and tend to separate the bottom 26 of the face 25 of the box 20 opposite it. The open face 19 can possibly be covered with a flexible diaphragm designed to prevent the intrusion of foreign bodies in the cassette 3. Such a diaphragm would not modify the operation of said cassette 3.

The sensitive zone 21 of the box 20 is arranged near the face 25 in order to be protected by the bottom 26 of the case 18. Thus, the sensitive zone 21, protected by the bottom 26, cannot directly enter into contact with an external object upon a shock due to handling.

Figure 3:
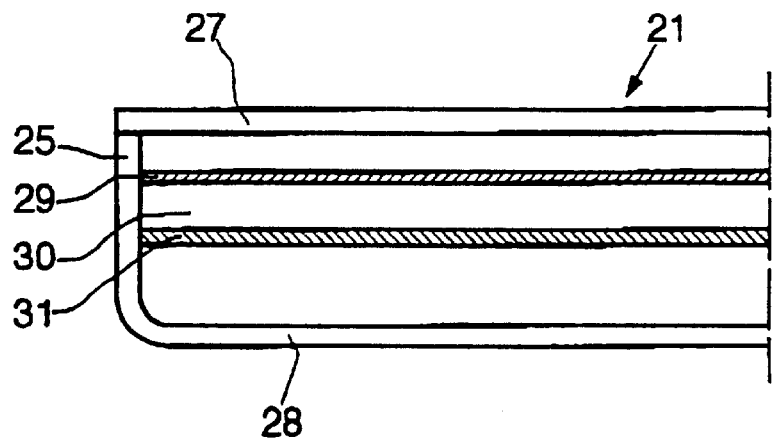
FIG. 3 is a schematic view in cross section of the sensitive area of the imaging device.

As illustrated in FIG. 3, the sensitive zone 21 comprises an upper wall 27 transparent to X-rays, a part of the face 25 and a lower wall 28. Arranged between the upper wall 27 and the lower wall 28 are a scintillator 29 capable of converting the X-rays into visible light, a fiber optic layer 30 intended for transfer of the visible light and a matrix camera 31 consisting of a plurality of charge transfer cells called CCD.

In operation, the X-rays are emitted by the source 7 (FIG. 1), cross the holding platform 2a of the puncture system 2, the X-rayed organ, the cassette holder and the upper wall 27 of the sensitive zone 21 of the cassette and pass into the scintillator 29 which, on the reception of X-rays, emits the visible light transferred to the matrix camera 31 by the fiber optic layer 30.

Figure 4:
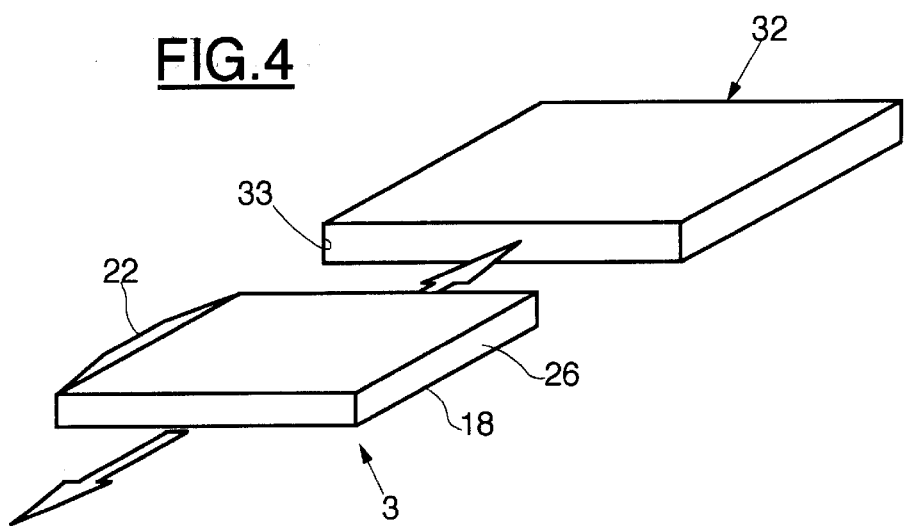
FIG. 4 is a view in perspective of an imaging device in proximity to its housing.

The matrix camera 31 makes possible the conversion of the information received in the form of visible light into information in the form of an electric signal transmitted by the electric cable 13 to the control and processing means 4 (FIG. 4). The sensitive zone 21 being, in operation, situated on the edge of the cassette 3, an image is obtained, which can include the areas of the breast closest to the patient's chest.

The puncture system 2 illustrated in FIG. 1 and the cassette holder used on diagnostic examinations each include a housing 32 (FIG. 4) capable of receiving a cassette 3. The cassette 3 can enter or exit from the housing 32 in the direction indicated by the arrows. The housing 32 is equipped with guide means, not represented, appropriate for the cassette 3. The cassette 3 is presented at the entrance to the housing 32, so that one of the narrow sides 33 of the housing 32 comes in contact with the projecting part 22 opposite the bottom 26 of the case 18. On insertion of the cassette 3 in the housing 32, the narrow side 33 comes to bear on the projecting part 22 and causes the retraction of the projecting part 22 in the case 18 by squeezing the springs 24 without the latter abutting.

Figure 5A:
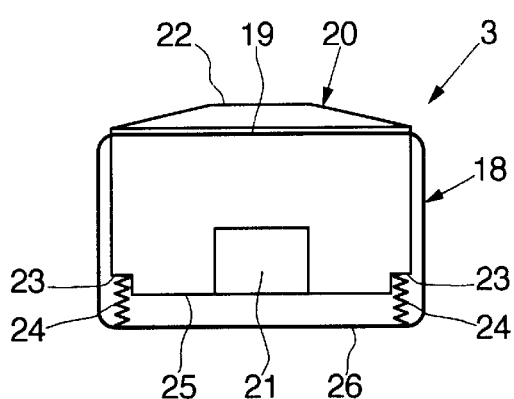
FIG. 5a is a top view in elevation of the imaging device in rest position.
Figure 5B:
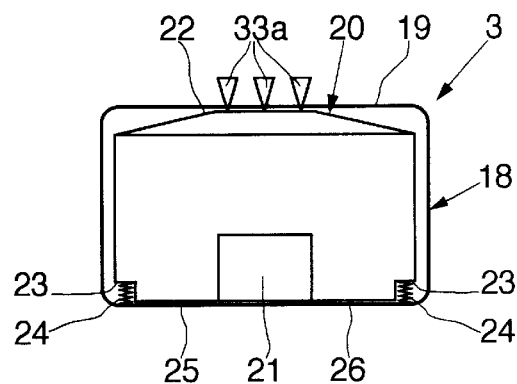
FIG. 5b is a top view of the imaging device inserted in its housing.

This translation movement is schematically illustrated in FIGS. 5a and 5b. It can be seen that, before the cassette 3 enters the housing 32, the sensitive zone 21 is separated from the bottom 26 of the case 18. On the other hand, after insertion of the cassette 3 in the housing 32 (FIG. 5b), a bearing portion 33a of the side 33 of the housing 32 comes to bear on the projecting portion 22 and causes its retraction in the case 18. The side 25 of the box 20 comes in contact with the bottom 26 of the case 18 and the sensitive zone 21 is thus in immediate proximity to the bottom 26 of the case 18, which makes it possible to carry out digital imaging satisfactorily.

Figure 6:
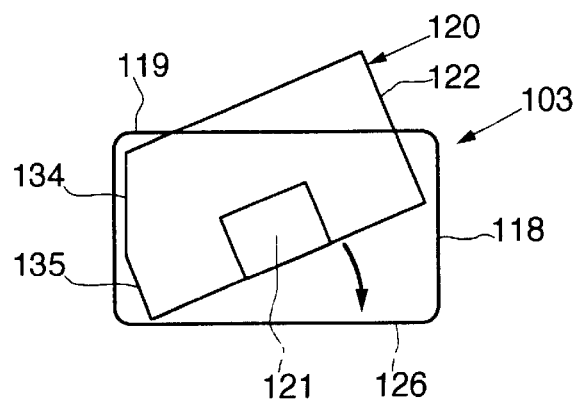
FIG. 6 is a top view in elevation of another embodiment of the imaging device.

In FIG. 6, the references of the elements similar to those of the previous figures have been increased by the number 100. The case 118 of the cassette 103 is unchanged. The box 120 contains a truncated corner 134 and a bearing corner 135. The box 120 is kept in permanent contact with the bottom 126 of the case 118 by the bearing corner 135. In rest position, the corner opposite the bearing corner 135 forms the projecting portion 122 under the effect of the elastic means not represented. The truncated corner 134 is in proximity to the wall of the case 118. On insertion in a housing provided for that purpose, the projecting portion 122 is lowered inside the case 118. The box 120 pivots in the direction indicated by the arrow, and the sensitive zone 121 is placed in proximity to the bottom 126 of the case 118.

A digital imaging cassette is thus made in an embodiment of the invention, which can be adapted to existing X-ray machines and is particularly well protected against damage caused by handling by the operators, thanks to the fact that case and box are mobile relative to one another and to the protection of the sensitive zone by the bottom of the case. If the case alone is damaged, it may be replaced, while keeping the same box. Now, the case is low in cost compared to the box and the sensitive zone. The costs of operation of the X-ray system are thus reduced.

In the embodiment of to the invention, one obtains an appreciable reduction of cost due to the damage to cassettes upon handling by an operator, the most cumbersome and sensitive part of the cassette being well protected.

Various modifications in steps and/or functions and/or structure of the disclosed embodiments of the invention may be made by one skilled in the art without departing from the scope and extent of the claims.

What is claimed is:

1. A radiation imaging device containing at least one sensing zone for detection of radiation comprising:
   means for protecting the zone by separating the zone from an edge of the device, the device being in a rest position; wherein the means for protection comprises a box bearing the zone being arranged inside the box and on one of the sides of the box;
   a case provided with an open face and capable of receiving the box, the side of the box with the zone being capable of coming in contact with the face of the case opposite the open face; and
   means arranged between a bottom of the case formed by the face opposite the open face and the side of the box with the zone for elastically separating the box from the bottom of the case rest position, the side of the box being capable of entering in contact with the bottom of the case, the means for elastically not abutting.

2. The device according to claim 1, wherein means for elastically separating is formed by at least one spring.

3. The device according to claim 2, wherein the box is capable of being moved by translation relative to the case.

4. The device according to claim 2, wherein the box is capable of being moved relative to the case by pivoting around a corner of the box in contact with the bottom of the case.

5. The device according to claim 1, wherein the side of the box opposite the side with the zone projects from the open face of the case, the device being in rest position.

6. The device according to claim 5, wherein the box is capable of being moved by translation relative to the case.

7. The device according to claim 5, wherein the box is capable of being moved relative to the case by pivoting around a corner of the box in contact with the bottom of the case.

8. The device according to claim 1, wherein the box is capable of being moved by translation relative to the case.

9. The device according to claim 1, wherein the zone includes a scintillator capable of converting the radiation into visible light radiation, an optic fiber and a CCD matrix camera.

10. A radiography system comprising:
    an imaging device containing X-ray detectors;
    means for protecting the X-ray detectors by separating the X-ray detectors from an edge of the device, the device being in rest position;
    means for X-ray emission;
    means for supporting the imaging device;
    an organ to be X-rayed being placed between the means for support and the means for emission;
    means for signal control and processing connected to the imaging device in order to read the images obtained;
    wherein the means for protection comprises a box bearing a zone being arranged inside the box and on one of the sides of the box;
    a case provided with an open face and capable of receiving the box, the side of the box with the zone being capable of coming in contact with the face of the case opposite the open face; and
    means arranged between a bottom of the case formed by the face opposite the open face and the side of the box with the zone for elastically separating the box from the bottom of the case rest position, the side of the box being capable of entering in contact with the bottom of the case, the means for elastically not abutting.

11. The radiography system according to claim 10, comprising means for conducting a biopsy of the X-rayed organ.

12. A device containing means for detecting a signal for conversion into an image, the device comprising:
    means for moving the means for detecting within the device between a first position and a second position, the first position being disposed at one edge of the device and the second position being disposed separated from the one edge of the device;
    wherein the device comprises a box supporting the means for detecting, the means for detecting being arranged inside the box and on one of the sides of the box;

a case provided with an open face and capable of receiving the box, the side of the box with the means for detecting being capable of coming in contact with the face of the case opposite the open face;

means arranged between the bottom of the case formed by the face opposite the open face and the side of the box integral with the means for detecting for elastically separating the box from the bottom of the case, the side of the box being capable of entering in contact with the bottom of the case, the means for elastically separating not in abutting relationship with the case.

13. The device according to claim 12 wherein the means for elastically separating comprises at least one spring.

14. The device according to claim 13 wherein the box is capable of being moved by translation relative to the case.

15. The device according to claim 12 wherein the side of the box opposite the side with the means for detecting projects from the open face of the case.

16. The device according to claim 15 wherein the box is capable of being moved by translation relative to the case.

17. The device according to claim 15 wherein the box is capable of being moved relative to the case by pivoting around a corner of the box in contact with the bottom of the case.

18. The device according to claim 12 wherein the box is capable of being moved by translation relative to the case.

19. The device according to claim 12 wherein the box is capable of being moved relative to the case by pivoting around a corner of the box in contact with the bottom of the case.

20. The device according to claim 12, wherein the means for detecting include a scintillator capable of converting X-rays into visible light radiation, an optic fiber and a CCD matrix camera.

21. The device according to claim 12 wherein the device is intended to provide a digital image.

22. A radiography system comprising:

a device containing means for detecting a signal for conversion into an image;

means for protecting the means for detecting by separating the means for detecting from an edge of the device;

means for radiation emission;

means for supporting an imaging device;

means for signal control and processing connected to the imaging device in order to read the images obtained;

means for moving the means for detecting within the device between a first position and a second position, the first position being disposed at the one edge of the device and the second position being disposed separated from the one edge of the device;

wherein the device comprises a box supporting the means for detecting, the means for detecting being arranged inside the box and on one of the sides of the box;

a case provided with an open face and capable of receiving the box, the side of the box with the means for detecting being capable of coming in contact with the face of the case opposite the open face; and means arranged between the bottom of the case formed by the face opposite the open face and the side of the box integral with the means for detecting for elastically separating the box from the bottom of the case, the side of the box being capable of entering in contact with the bottom of the case, the means for elastically separating not in abutting relationship with the case.

23. The radiography system according to claim 22 comprising means for conducting a biopsy.

24. A removable radiation imaging device containing at least one sensitive zone for detecting radiation comprising:

means for protecting the zone by separating the zone from an edge of the device, the device being in a rest position;

wherein the means for protecting comprises a box bearing the zone, the zone being arranged inside the box and on one of the sides of the box;

a case provided with an open face and capable of receiving the box, the side of the box with the zone being capable of coming into contact with the face of the case opposite to the open face;

means for separating the box from a bottom of the case rest position, the bottom formed by the face opposite to the open face of the box and the side of the box with the zone by pivoting the box around a corner of the box in contact with the bottom of the case.

25. The device according to claim 25 wherein the side of the box opposite the side with the zone projects from the open face of the case, when the device being in rest position.

26. The device according to claim 25, wherein the zone includes a scintillator capable of converting the radiation into visible light radiation, an optic fiber and a CCD matrix camera.

* * * * *